(12) United States Patent
Shokoohi

(10) Patent No.: US 6,869,427 B1
(45) Date of Patent: Mar. 22, 2005

(54) LED FIXATION DEVICE FOR TOPICAL ANESTHESIA EYE SURGERY

(76) Inventor: Kamran K. Shokoohi, 341 Golfview Dr., Saginaw, MI (US) 48603

( * ) Notice: Subject to any disclaimer, the term of this patent is extended or adjusted under 35 U.S.C. 154(b) by 0 days.

(21) Appl. No.: 09/855,012

(22) Filed: May 14, 2001

Related U.S. Application Data

(60) Provisional application No. 60/211,838, filed on Jun. 15, 2000.

(51) Int. Cl.$^7$ ................................................ A61F 9/007
(52) U.S. Cl. ..................... 606/1; 606/2; 606/5; 606/10; 607/88; 607/91; 602/2; 604/20; 351/222
(58) Field of Search ............................. 602/2; 604/20; 606/5, 10, 9, 1, 2; 607/88, 91; 612/2; 367/27; 2/455; 351/222–225

(56) References Cited

U.S. PATENT DOCUMENTS

| | | | | |
|---|---|---|---|---|
| 4,796,987 A | * | 1/1989 | Linden | ........................ 351/158 |
| 5,266,977 A | * | 11/1993 | Linden | ........................ 351/47 |
| 5,293,532 A | * | 3/1994 | Marshall | ..................... 351/222 |
| 5,445,608 A | * | 8/1995 | Chen et al. | .................... 604/20 |
| 5,474,528 A | * | 12/1995 | Meserol | ....................... 604/20 |
| 5,585,871 A | * | 12/1996 | Linden | ........................ 351/158 |
| 5,884,340 A | * | 3/1999 | Chen et al. | ..................... 2/455 |
| 6,033,396 A | * | 3/2000 | Huang et al. | |
| 6,164,789 A | * | 12/2000 | Unger et al. | ................... 362/27 |
| 6,319,273 B1 | * | 11/2001 | Chen et al. | .................... 607/88 |
| 6,325,792 B1 | * | 12/2001 | Swinger et al. | ................ 606/4 |

* cited by examiner

*Primary Examiner*—David M. Shay
(74) *Attorney, Agent, or Firm*—Harness, Dickey & Pierce, P.L.C.

(57) ABSTRACT

An LED fixation device that is secured to a patient's face and covers the patient's fellow eye during eye surgery to provide a lighted fixation target. The fixation device includes an eye shield, a battery, a switch and an LED light source secured to the eye shield. The light source is switched on, and the patient is directed to look at the light source during the surgical procedure. The eye shield can be made of any suitable material, such as plastic and paper, and can be disposable.

13 Claims, 2 Drawing Sheets

LED FIXATION DEVICE FOR TOPICAL ANESTHESIA EYE SURGERY

CROSS-REFERENCE TO RELATED APPLICATIONS

This application claims priority from U.S. Provisional Application No. 60/211,838, titled LED Fixation Device for Topical Anesthesia Eye Surgery, filed Jun. 15, 2000.

BACKGROUND OF THE INVENTION

1. Field of the Invention

This invention relates generally to a lighted fixation device and, more particularly, to an LED fixation device for use in topical anesthesia eye surgery, such as clear cornea cataract surgery.

2. Discussion of the Related Art

Cataract or opacification of the lens in the human eye is a prevalent medical condition and a major cause of preventable blindness worldwide. The exact etiology of this condition is unknown, but cataracts are usually thought to be changes that occur in the lens as a result of aging. Cataracts are also seen in certain ocular or systemic diseases, in ocular trauma and after exposure to some systemic drugs.

Currently cataracts can only be treated surgically. The current treatment involves surgically removing the human lens and implantating an intraocular lens. Small incision techniques, state of the art biomedical instrumentation and safe and stable intraocular lenses have combined to make cataract surgery one of the safest and fastest procedures in medicine. Cataract extraction and lens implantation can be achieved with minimum pain and discomfort. With the advent of small, sutureless clear corneal incisions, and by using foldable intraocular lenses, cataract surgery is performed with less trauma, faster and with greater control, and has allowed some surgeons to use topical anesthesia as the procedure of choice. Pediatric cases are mostly performed under general anesthesia, however.

With the improvement of surgery techniques and equipment, most major complications related to cataract surgery are on the decline. However, complications associated with regional block anesthesia still present a significant problem. For regional block anesthesia procedures, it is common to significantly sedate the patient in combination with the block. This level of sedation can cause respiratory compromise. Systemic complications include allergic reactions, systemic toxicity, intrarterial injection and optic nerve sheath injection. For an experienced surgeon, these complications are rare, but they can and do happen.

Topical anesthesia obviates most medical contraindications to cataract surgery. Topical anesthesia avoids potential complications of retrobulbar or peribulbar block which can include globe perforations, retrobulbar hemorrhage, optic nerve atrophy, retinal vascular occlusion and ptosis. Topical anesthesia gives an extra margin of safety for the medically compromised patients. Topical anesthesia also allows for a fast visual rehabilitation time. Most patients may go home from the procedure without a patch and see clearly just 30 minutes after phaco with a clear corneal incision under topical anesthesia.

Topical anesthesia does not require special training or a learning curve, and can be given to the patient in the preoperative area by staff along with dilating drops. It can be repeated at any time during the preoperative period prior to making the incision. Patient anxiety can usually be easily controlled with communication. Assuring the patient that there will be no pain and reporting the progress of the procedure will usually calm the patient's anxiety. Mild sedation can be used as an adjunct if needed.

The use of topical anesthesia during eye surgery does have certain disadvantages, however. Perhaps the most important disadvantage for a surgeon is eye movement during various stages of cataract surgery. Eye movement, and most importantly eye positioning, is crucial for most stages of the surgery. Undesired eye movement or position might require extra steps that may cause introperative or postoperative complications. Patients who are unable to cooperate or follow commands, including patients with dementia, nystagmus, deafness or inability to communicate because of language, do better under a regional block with IV sedation.

Even for cooperative and preoperatively well-selected patients, it sometimes becomes difficult to maintain a desirable eye position at the start or during the surgical procedure. The bright microscope light is sometimes hard to look at directly and some patients try to avoid it. Positioning the microscope to avoid direct illumination might compromise obtaining a good red reflect that might be necessary for some critical steps. Furthermore, since the fellow eye is usually covered, patients sometimes lose orientation to space and are not able to follow surgeon's directional commands to realign the eye, such as looking down, left or any other direction. Patients can move their eye between stages of surgery, and this requires another command by the surgeon to realign the eye or to reposition the microscope or manually maintain the eye position using an instrument. The latter requires the surgeon to perform extra manipulation of the eye.

What is needed is a procedure or device that helps a patient maintain his or her eye directed in a preferable direction during eye surgery, and that does not employ anesthesia or sedation. It is therefore an object of the present invention to provide such a device.

SUMMARY OF THE INVENTION

In accordance with the teachings of the present invention, a lighted fixation device is disclosed that reduces or eliminates eye movement during topical anesthesia cataract surgery. The fixation device is secured to the patient's face so that it is positioned over the patient's fellow eye during the surgery. The fixation device includes an LED that provides an observation target for the fellow eye. When the fellow eye is looking in the proper direction, the conjugate eye undergoing the cataract extraction will be looking at a desired position in the field of the microscope. Furthermore, this allows position maintenance and interactive realignment during surgery by having the patient fixate on the LED with the fellow eye. If fixation is lost, the patient is told to simply look at the LED. This eliminates the need to communicate eye orientation, such as left, right, etc., with the patient.

Additional objects, advantages, and features of the present invention will become apparent from the following description and appended claims, taken in conjunction with the accompanying drawings.

DETAILED DESCRIPTION OF THE PREFERRED EMBODIMENTS

The following discussion of the preferred embodiments directed to a lighted fixation device for use in topical anesthesia eye surgery is merely exemplary in nature, and is in no way intended to limit the invention or its applications or uses.

Figure 1:
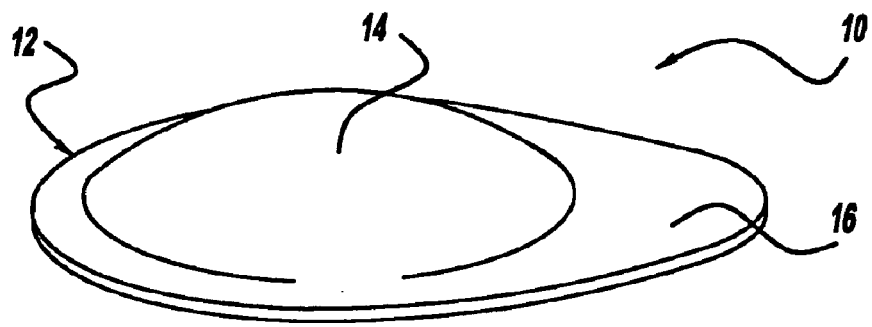
FIG. 1 is a perspective view of a fixation device for providing a lighted fixation target during eye surgery, according to an embodiment of the present invention.
Figure 2:
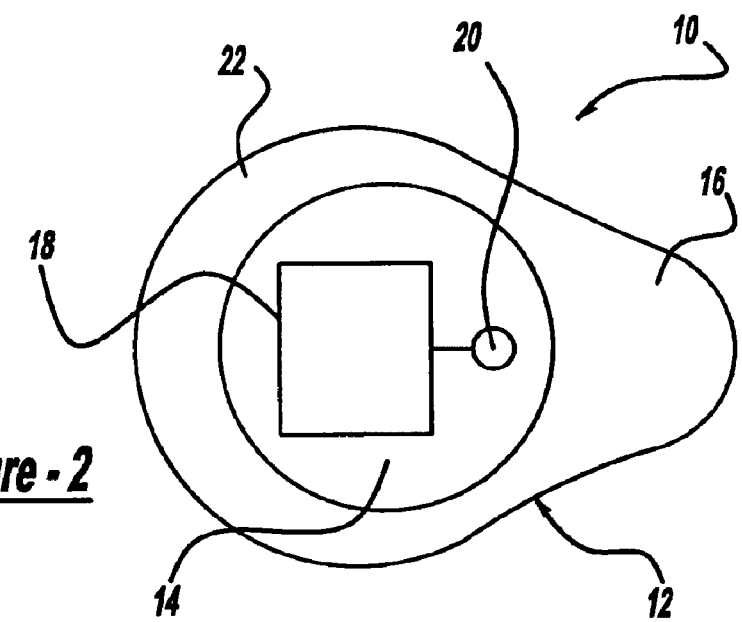
FIG. 2 is a back view of the fixation device shown in FIG. 1.

FIG. 1 is a perspective view and FIG. 2 is a back plan view of a fixation device 10, according to an embodiment of the present invention. The fixation device 10 is a medical device to be used during eye surgery, such as cataract surgery, using a topical anesthesia. The fixation device 10 includes an eye shield or cover 12 made of any suitable material, such as plastic, paper, etc., for covering the fellow eye that is not being operated on during the eye surgery. The cover 12 is taped to the patient's face and is aligned with the fellow eye during the surgical procedure. The cover 12 includes a protruding dome portion 14 and a rim portion 16. The rim portion 16 has the shape of a "tear drop" in this design, but can take on any shape suitable for the purposes described herein.

The device 10 includes electronics 18 and a light source 20 mounted to a back surface 22 of the dome portion 14. The light source 20 can be any light source suitable for the purposes described herein, such as an LED. The electronics 18 and the light source 20 can be mounted to the cover 12 by any suitable securing device, such as glue. Alternately, the electronics 18 can be mounted to other locations on or within the cover 12 to provide a more aesthetically pleasing appearance. The light source 20 is positioned at a location on the fixation device 10 so that when the cover 12 is secured to the patients face, the light source 20 is positioned at a desirable location relative to the patient's fellow eye.

Figure 3:
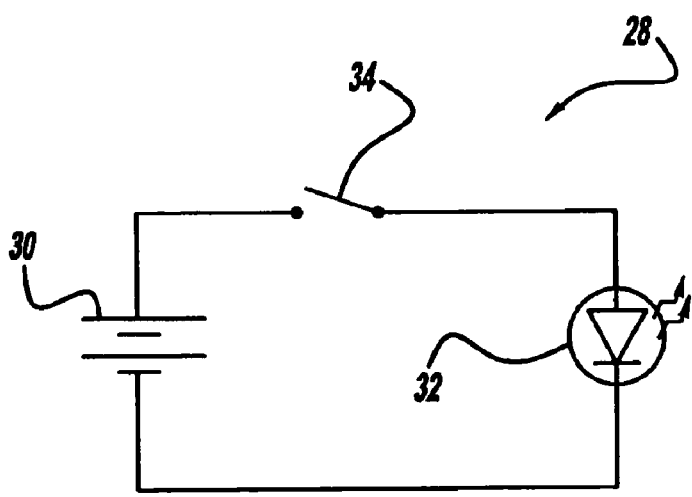
FIG. 3 is a schematic diagram of the electronics used in the fixation device shown in FIG. 1.

FIG. 3 is a schematic diagram 28 of the electrical circuit elements in the electronics 18. In this design, the circuit includes a DC power source 30, such as batteries, an LED 32, acting as the source 20, and a switch 34 for turning the LED 32 on and off. In one embodiment, the LED is red, but other colors can be used within the scope of the present invention. Other circuit elements, such as logic elements, can also be provided in a more sophisticated device within the scope of the present invention.

The following specifications for the fixation device 10 are provided by way of a non-limiting example.

| | |
|---|---|
| LED brightness | 5.2 mcd (milli-candles) |
| Peak emission wavelength | 697 nm (nano-meters) |
| Viewing angle | 40 degrees |
| Forward voltage | 5.2 Volts maximum |
| Forward current | 2.0 mA (milli-ampers) |
| Power supply | 1.5–3.0 Volts |

The fixation device 10 can be made with commercially available parts, including a commercially available LED. In one embodiment, the device 10 uses two 1.5 Volt dry cell batteries in series mounted on an eye shield, and is reusable. However, the device 10 can be made to be disposable. A disposable device might be an advantage in the operating room since medically sterile products are necessary. Therefore, the entire device 10 can be made for one time use as a recyclable unit.

Figure 4A:
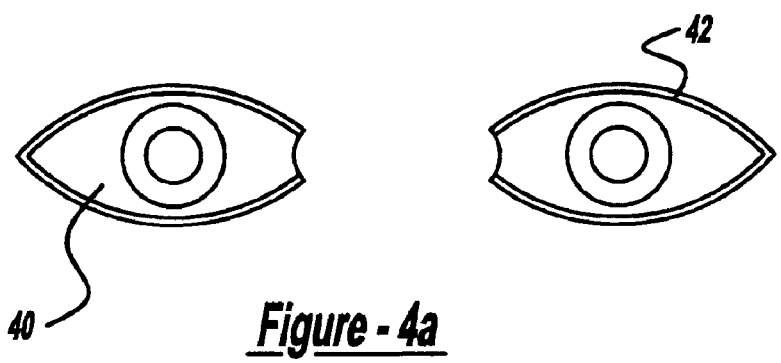
FIG. 4(a) is a representation of the eyes of a patient.
Figure 4B:
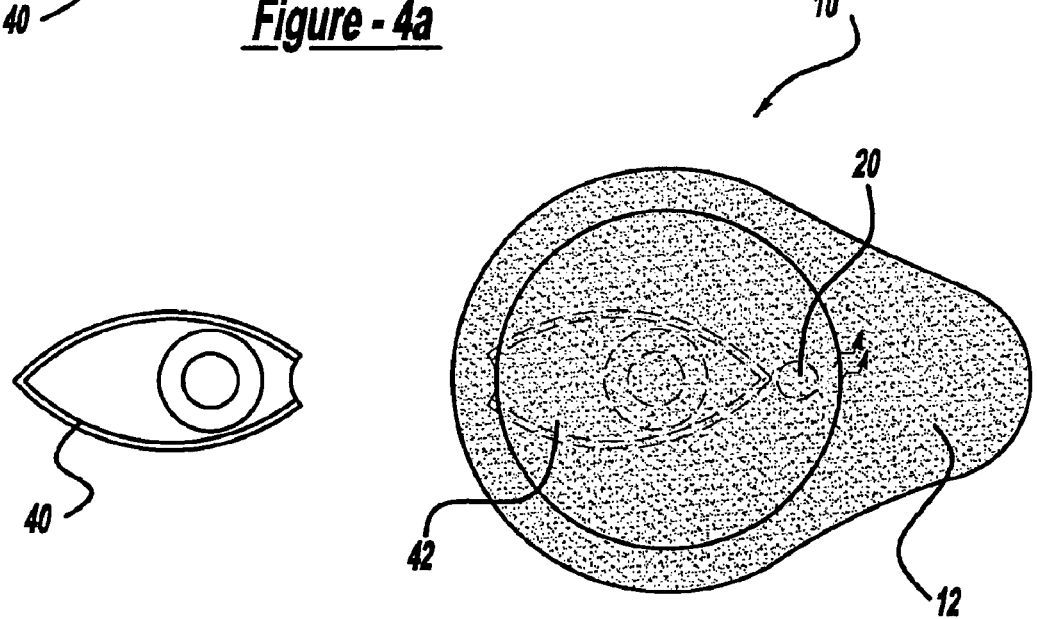
FIG. 4(b) is the representation of the eyes of a patient shown in FIG. 4(a), where the fixation device of the invention is positioned over the fellow eye.

FIG. 4(a) illustrates a right eye 40 and a left eye 42 of a patient, where the right eye 40 is the one having cataract surgery and the left eye is the fellow eye. FIG. 4(b) shows the fixation device 10 positioned over the left eye 42, where the source 20 is opposite the right eye. When the patient looks at the source 20 in this position, both eyes 40 and 42 will move to the left, and the right eye 40 will be in the desirable location for surgery.

The device 10 is turned on and is placed in front of the patient's fellow eye 42 prior to surgery. This can be achieved by the surgeon or the operating room staff. The patient is instructed to look at the source 20 to determine if the patient's eye 40 moves to the proper location for surgery. The position of the device 10 can be adjusted until the patient's eyes are looking in the desired direction for the surgical procedure. The device 10 is then secured to the patient at this location. The eye 40 is prepped and the surgical field is draped in a usual sterile ophthalmic manner. The operating microscope light is then turned on and the microscope is focused on the eye 40 in the usual manner. The device 10 and the eye 42 are covered under the sterile drapes. Patients are asked to look at the source 20 when commanded by the surgeon or when they open their eye under the drape. Patients are instructed to blink or close the eye 42 under the device 10 as much as needed. At the end of the procedure the device 10 is discarded or recycled as needed.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A fixation device for directing an eye of a patient during a surgical procedure, said fixation device comprising:

an eye shield including a relieved portion that covers an eye of a patient;

a single light source mounted on said eye shield to define a target point which fixates said eye at said target point;

an electrical circuit mounted on said eye shield and coupled to said single light source for operating said single light source in an illuminated state; and a rim portion extending from said relieved portion that receives an adhesive for securing said eye shield relative to said patient.

2. The fixation device according to claim 1 wherein the light source is an LED.

3. The fixation device according to claim 1 wherein the electrical circuit includes an electrical switch for turning the light source on.

4. The fixation device according to claim 1 wherein the electrical circuit includes at least one battery for providing DC power to the light source.

5. The fixation device according to claim 1 wherein the eye shield is made of a material selected from the group consisting of plastic and paper.

6. The fixation device according to claim 1 wherein said rim portion has a teardrop shape.

7. A fixation device for directing an eye of a patient during a surgical procedure, said fixation device comprising:

an eye shield including a dome and a rim extending from said dome, said rim receiving an adhesive for securing said eye shield to a patient's face;

a single light source mounted on said dome; and an electrical circuit mounted on said eye shield and including a battery and a switch electrically coupled to said single light source, said switch being activated to provide battery power to said single light source to illuminate said single light source and focus said eye at said single light source during a surgical procedure.

8. The fixation device of claim 7 wherein said rim comprises a substantially planar portion extending laterally from said dome.

9. The fixation device of claim 7 wherein said dome is a segment of a sphere.

10. The fixation device according to claim 7 wherein the eye shield is made of a material selected from the group consisting of plastic and paper.

11. The fixation device according to claim 7 wherein said rim has a teardrop shape.

12. The fixation device of claim 7 wherein said dome has an inside surface and said light source is mounted on said inside surface.

13. The fixation device of claim 7 wherein said light source is a light emitting diode.

* * * * *